US00PP31975P3

(12) United States Plant Patent
Post

(10) Patent No.: US PP31,975 P3
(45) Date of Patent: Jul. 14, 2020

(54) ***CHRYSANTHEMUM* PLANT NAMED 'DLFBRI1'**

(50) Latin Name: ***Chrysanthemum* X *morifolium***
Varietal Denomination: DLFBRI1

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 16/501,363

(22) Filed: Mar. 29, 2019

(65) Prior Publication Data

US 2019/0307044 P1 Oct. 3, 2019

Related U.S. Application Data

(60) Provisional application No. 62/761,600, filed on Mar. 30, 2018.

(51) Int. Cl.
*A01H 5/02* (2018.01)
*A01H 6/14* (2018.01)

(52) U.S. Cl.
USPC ..... Plt./288
CPC ..... *A01H 6/1424* (2018.05)

(58) Field of Classification Search
USPC ..... Plt./286, 287, 288
See application file for complete search history.

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'DLFBRI1', characterized by its upright plant habit; vigorous growth habit; relatively rapid growth rate; dark green-colored leaves; uniform and freely flowering habit; strong upright flowering stems with numerous inflorescences; and large decorative-type inflorescences with white-colored ray florets.

2 Drawing Sheets

Botanical designation: *Chrysanthemum* X *morifolium*.
Cultivar denomination: 'DLFBRI1'.

CROSS-REFERENCED TO CLOSELY RELATED APPLICATIONS

Title: Varieties of *Chrysanthemum* Plants
Applicant: Arie Gerard Post
Provisional application Ser. No. 62/761,600
Filed: Mar. 30, 2018

BACKGROUND OF THE INVENTION

The present invention relates to a new and distinct cultivar of *Chrysanthemum* plant, botanically known as *Chrysanthemum* X *morifolium*, commercially grown as a cut flower and hereinafter referred to by the name 'DLFBRI1'.

The new *Chrysanthemum* plant is a product of a planned breeding program conducted by the Inventor in Maasdijk, The Netherlands. The objective of the breeding program is to create new freely-flowering cut *Chrysanthemum* plants with attractive inflorescences, strong flowering stems and excellent postproduction longevity.

The new *Chrysanthemum* plant originated from a cross-pollination on Mar. 19, 2015 of a proprietary selection of *Chrysanthemum* x *morifolium* identified as code number DB 21697 as the female, or seed, parent with a proprietary selection of *Chrysanthemum* x *morifolium* identified as code number DB 26704 as the male, or pollen, parent. The new *Chrysanthemum* plant was discovered and selected as a single flowering plant from within the progeny of the stated cross-pollination in a controlled greenhouse environment in Maasdijk, The Netherlands on Oct. 9, 2015.

Asexual reproduction of the new *Chrysanthemum* plant by vegetative terminal cuttings since Oct. 9, 2015 has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFBRI1'. These characteristics in combination distinguish 'DLFBRI1' as a new and distinct *Chrysanthemum* plant:

1. Upright plant habit; vigorous growth habit.
2. Relatively rapid growth rate.
3. Dark green-colored leaves.
4. Uniform and freely flowering habit.
5. Strong upright flowering stems with numerous inflorescences.
6. Large decorative-type inflorescences with white-colored ray florets.

Plants of the new *Chrysanthemum* differ from plants of the female parent selection in the following characteristics:

1. Plants of the new *Chrysanthemum* have larger inflorescences than plants of the female parent selection.
2. Plants of the new *Chrysanthemum* flower five days earlier than plants of the female parent selection.
3. Ray florets of plants of the new *Chrysanthemum* are twisting whereas ray florets of plants of the female parent selection are slightly incurved.

Plants of the new *Chrysanthemum* differ from plants of the male parent selection in the following characteristics:

1. Plants of the new *Chrysanthemum* have larger inflorescences than plants of the male parent selection.
2. Ray florets of plants of the new *Chrysanthemum* are twisting whereas ray florets of plants of the male parent selection are straight and not twisting.

Plants of the new *Chrysanthemum* can be compared to plants of *Chrysanthemum* X *morifolium* 'Delibaltica', not patented. In side-by-side comparisons plants of the new *Chrysanthemum* differ primarily from plants of 'Delibaltica' in the following characteristics:

1. Plants of the new *Chrysanthemum* have smaller inflorescences than plants of 'Delibaltica'.
2. Plants of the new *Chrysanthemum* flower five days earlier than plants of 'Delibaltica'.
3. Ray florets of plants of the new *Chrysanthemum* are twisting whereas ray florets of plants of 'Delibaltica' are straight and not twisting.
4. Developing ray florets of plants of the new *Chrysanthemum* are white in color whereas developing ray florets of plants of 'Delibaltica' are green in color.

Plants of the new *Chrysanthemum* can be compared to plants of *Chrysanthemum* X *morifolium* 'Zembla', disclosed in U.S. Plant Pat. No. 14,052. In side-by-side comparisons plants of the new *Chrysanthemum* differ primarily from plants of 'Zembla' in the following characteristics:

1. Plants of the new *Chrysanthemum* have larger inflorescences than plants of 'Zembla'.
2. Plants of the new *Chrysanthemum* flower five days earlier than plants of 'Zembla'.
3. Ray florets of plants of the new *Chrysanthemum* are twisting whereas ray florets of plants of 'Zembla' are slightly incurved.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'DLFBRI1' grown as a spray-type.

The photograph on the second sheet comprises close-up views of the lower (top of the photographic sheet) and upper surfaces (bottom of the photographic sheet) of typical inflorescences and leaves of 'DLFBRI1'.

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 22° C., night temperatures ranged from 20° C. to 25° C. and light levels averaged 8 klux. Plants were grown as single-stem plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFBRI1'.

Parentage:

*Female, or seed, parent.*—Proprietary selection of *Chrysanthemum* X *morifolium* identified as code designation DB 21697, not patented.

*Male, or pollen, parent.*—Proprietary selection of *Chrysanthemum* X *morifolium* identified as code designation DB 26704, not patented.

Propagation:

*Type.*—Terminal vegetative cuttings.

*Time to initiate roots, summer.*—About six days at temperatures about 24° C.

*Time to initiate roots, winter.*—About eight days at temperatures about 22° C.

*Time to produce a rooted young plant, summer.*—About twelve days at temperatures about 24° C.

*Time to produce a rooted young plant, winter.*—About two weeks at temperatures about 22° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous decorative-type cut flower that is typically grown as a single stem spray-type; upright plant habit; vigorous growth habit and rapid growth rate.

*Plant height, soil level to top of foliar plane.*—About 76.2 cm.

*Plant height, soil level to top of inflorescence plane.*—About 83 cm.

*Plant (spray) diameter.*—About 19.2 cm.

*Flowering stem length.*—About 75.6 cm.

*Flowering stem diameter.*—About 6.5 mm.

*Flowering stem internode length.*—About 3 cm.

*Flowering stem strength.*—Strong.

*Flowering stem aspect.*—Erect.

*Flowering stem texture and luster.*—Moderately pubescent; slightly glossy.

*Flowering stem color, developing.*—Close to 144A, at the internodes, close to 146B.

*Flowering stem color, developed.*—Close to 146B and 147C to 147D.

*Leaf description.*—Arrangement: Alternate; simple. Length: About 12.8 cm. Width: About 8.2 cm. Shape: Ovate. Apex: Short apiculate. Base: Attenuate. Margin: Palmately lobed, coarsely crenate; sinuses convergent and medium to deep in depth. Texture and luster, upper surface: Moderately pubescent, not rugose; moderately velvety; very slightly glossy. Texture and luster, upper surface: Densely pubescent, prominent venation; slightly velvety; matte. Venation pattern: Pinnate, reticulate. Color: Developing leaves, upper surface: Slightly darker than 143A. Developing leaves, lower surface: Close to 146B. Fully developed leaves, upper surface: Close to NN137A; venation, close to 146B. Fully developed leaves, lower surface: Close to 147B; venation, close to 147C to 147D. Petioles: Length: About 1.6 cm. Diameter: About 3 mm by 4.5 mm. Strength: Moderately strong. Texture and luster, upper and lower surfaces: Densely pubescent; slightly glossy. Color, upper surface: Close to 147C; edges, close to NN137B. Color, lower surface: Close to 147C; edges, close to 147B. Stipules: Quantity and appearance: Two leafy stipules, opposite, at the petiole attachment to the stem. Length: About 5 mm. Width: About 7 mm. Shape: Flabellate. Texture and luster, upper surface: Moderately pubescent; very slightly glossy. Texture and luster, lower surface: Densely pubescent; matte. Color, upper surface: Close to NN137A. Color, lower surface: Close to 147B.

Inflorescence description:

*Appearance.*—Decorative-type inflorescence form with oblanceolate-shaped ray florets and tubular disc florets (disc florets are inconspicuous); inflorescences borne perpendicular to peduncles and face mostly upright to slightly outwardly; ray and disc florets develop acropetally on a capitulum.

*Fragrance.*—Faintly fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 47 days later when grown as a spray-type.

*Postproduction longevity.*—Good postproduction longevity; in an interior environment, inflorescences and foliage will maintain good color and substance for about two weeks; inflorescences persistent.

*Quantity of inflorescences.*—Freely flowering habit; when grown as a spray-type, about 20 inflorescences develop per flowering stem.

*Inflorescence size.*—Diameter: About 10.5 cm. Depth (height): About 3.8 cm. Disc diameter: About 4 mm.

*Receptacles.*—Height: About 4 mm. Diameter: About 5 mm. Shape: Flattened globular. Color: Close to 148D.

*Inflorescence buds.*—Height: About 1.4 cm. Diameter: About 1.4 cm. Shape: Globular. Texture and luster: Distally, smooth and glabrous; proximally, sparsely pubescent; very slightly glossy. Color: Distally, close to 157D (immature ray florets); proximally, close to 143A.

*Ray florets.*—Quantity and arrangement: About 150 arranged in about six whorls. Length: About 5.1 cm. Width: About 1.1 cm. Shape: Oblanceolate; twisting, slightly carinate. Apex: Acute. Base: Attenuate. Margin: Entire; slightly undulate. Aspect: Initially upright to about 80° from vertical. Texture and luster, upper surface: Smooth, glabrous; moderately velvety; matte. Texture and luster, lower surface: Smooth, glabrous; moderately velvety; slightly glossy. Color: When opening, upper and lower surfaces: Initially, close to 157D, then close to NN155D. Fully opened, upper and lower surfaces: Close to NN155D; venation, close to NN155D; color does not change with development.

*Disc florets.*—Quantity and arrangement: About ten spirally arranged in two or three whorls at the center of the receptacle; disc florets inconspicuous. Length: About 7 mm. Diameter: About 1.75 mm. Shape: Lower 67% fused into a tube; upper 33% free. Apex: Narrowly acute. Margin: Entire. Texture and luster, inner and outer surfaces: Smooth, glabrous; glossy. Color, when opening, inner and outer surfaces: Apex: Close to N144B. Mid-section: Close to 14C. Base: Close to 145C to 145D. Color, fully opened, inner and outer surfaces: Apex: Close to 2B. Mid-section: Close to 14C to 14D. Base: Close to 145C to 145D.

*Involucral bracts.*—Quantity and arrangement: About 28 arranged in three whorls. Length: About 1 cm. Width: About 4 mm. Shape: Ovate. Apex: Obtuse. Base: Cuneate. Margin: Entire. Texture and luster, upper surface: Smooth, glabrous; glossy. Texture and luster, lower surface: Densely pubescent; slightly glossy. Color, upper surface: Close to 144A; margins, translucent, and close to 157D; apices, close to N199A. Color, lower surface: Close to 137A to 137B; margins, translucent, close to 157D; apices, close to N199A.

*Peduncles.*—Length, terminal peduncle: About 3.2 cm. Diameter, terminal peduncle: About 3.5 mm. Length, third peduncle: About 4.3 cm. Diameter, terminal peduncle: About 3 mm. Strength: Strong. Aspect, terminal peduncle: Mostly upright. Aspect, third peduncle: About 40° from the flowering stem axis. Texture and luster: Densely pubescent; matte. Color: Close to between 144A and 146A.

*Reproductive organs.*—Androecium: Present on disc florets only. Quantity: About five per floret. Filament length: About 3 mm. Filament color: Close to 150C. Anther size: About 0.5 mm by 2 mm. Anther shape: Narrowly oblong. Anther color: Close to 13A. Pollen amount: Scarce. Pollen color: Close to 17B. Gynoecium: Present on both ray and disc florets. Quantity: One per floret. Pistil length: About 5.5 mm. Style length: About 5 mm. Style color: Close to N144B. Stigma diameter: About 1.5 mm. Stigma shape: Cleft, decurrent. Stigma color: Close to 2B. Ovary color: Close to 145B to 145C.

*Seeds and fruits.*—To date, seed and fruit production have not been observed on plants of the new *Chrysanthemum.*

Pathogen & pest resistance: Plants of the new *Chrysanthemum* have been observed to be resistant to *Fusarium* Wilt (*Fusarium oxysporum f.* sp. *chrysanthemi*). To date, resistance to pests and other pathogens common to *Chrysanthemum* plants has not been observed on plants of the new *Chrysanthemum* grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFBRI1' as illustrated and described.

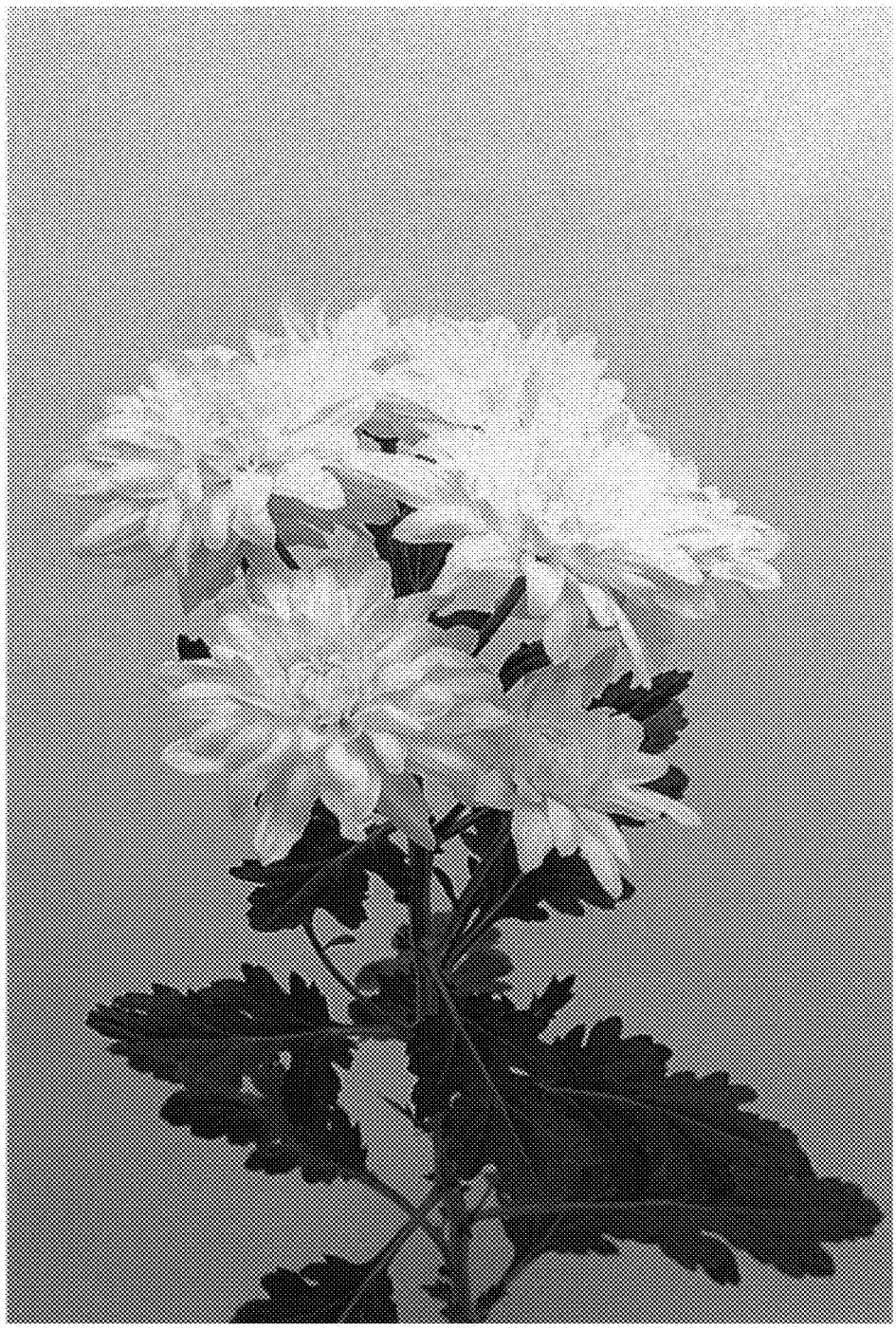

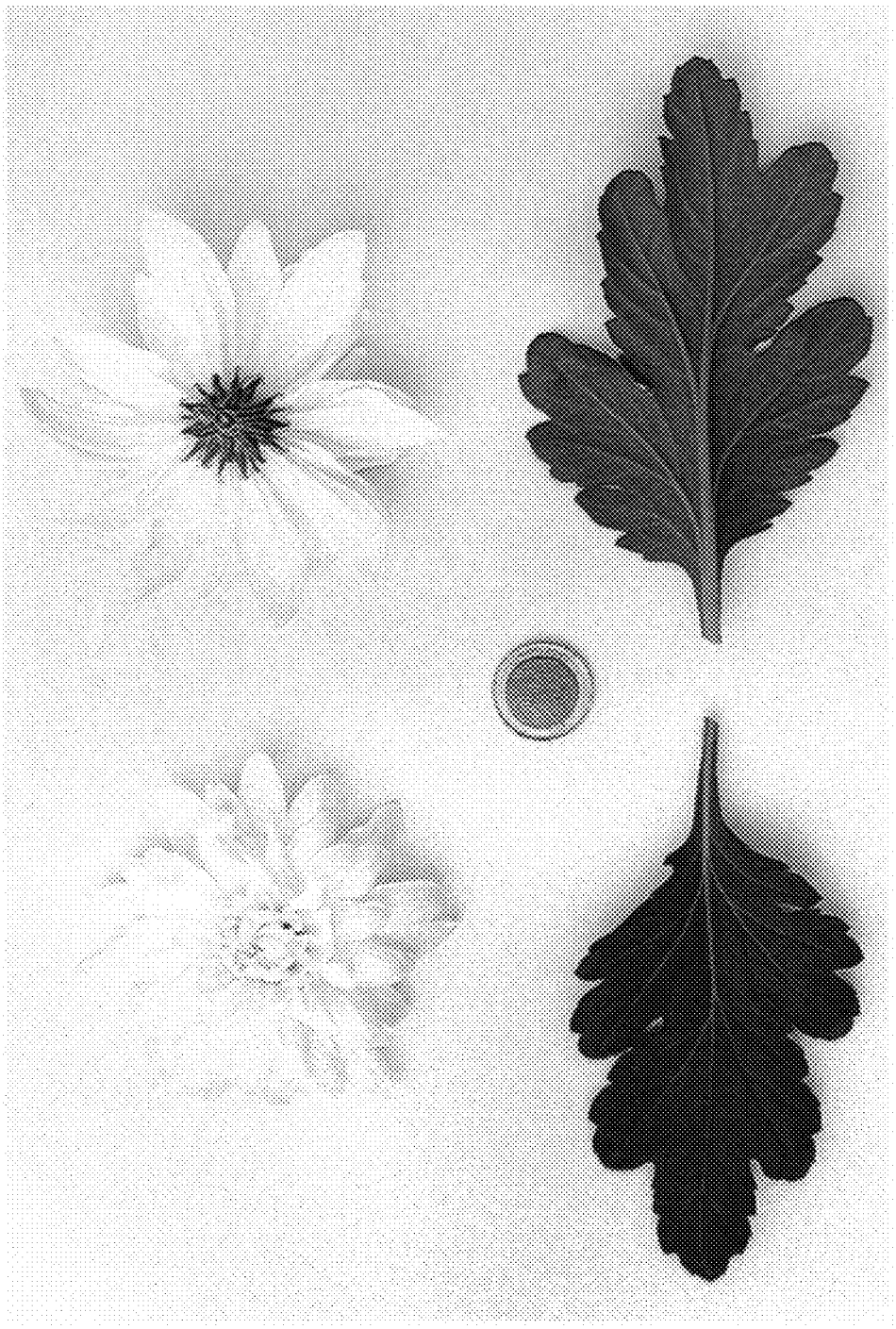

* * * * *